United States Patent [19]

Lambert et al.

[11] 4,105,922
[45] Aug. 8, 1978

[54] CT NUMBER IDENTIFIER IN A COMPUTED TOMOGRAPHY SYSTEM

[75] Inventors: Thomas W. Lambert, Dousman; James Edward Blake, New Berlin, both of Wis.

[73] Assignee: General Electric Company, Schenectady, N.Y.

[21] Appl. No.: 786,528

[22] Filed: Apr. 11, 1977

[51] Int. Cl.² .................. A61B 6/02; G01N 23/08
[52] U.S. Cl. ........................... 250/495 T; 250/369
[58] Field of Search .................. 250/445 T, 369, 252

[56] References Cited

U.S. PATENT DOCUMENTS 4,052,618  10/1977  Hounsfield .................. 250/445 T Primary Examiner—Alfred E. Smith
Assistant Examiner—T. N. Grigsby
Attorney, Agent, or Firm—Ralph G. Hohenfeldt

[57] ABSTRACT

In computed tomography, a computer calculates CT numbers corresponding with the X-ray attenuation by elemental volumes in a body undergoing an X-ray beam scan. Analog signals corresponding with the sequence of CT numbers modulate a raster scanned cathode ray tube to produce a display of the image. Means are provided for controlling the display tube to display elements within a range of CT numbers or gray scale window. New means are provided for causing zones in the image corresponding with picture elements near the selected level or center of the gray scale to blink from gray to white such that when the level is set to correspond with a gray scale level of interest, the blinking zones will have CT numbers corresponding with the level setting. This permits identification of the CT numbers of the zones. The blink mode may be activated while the full image is displayed on the screen and zones of interest may be visualized in the total picture.

5 Claims, 3 Drawing Figures

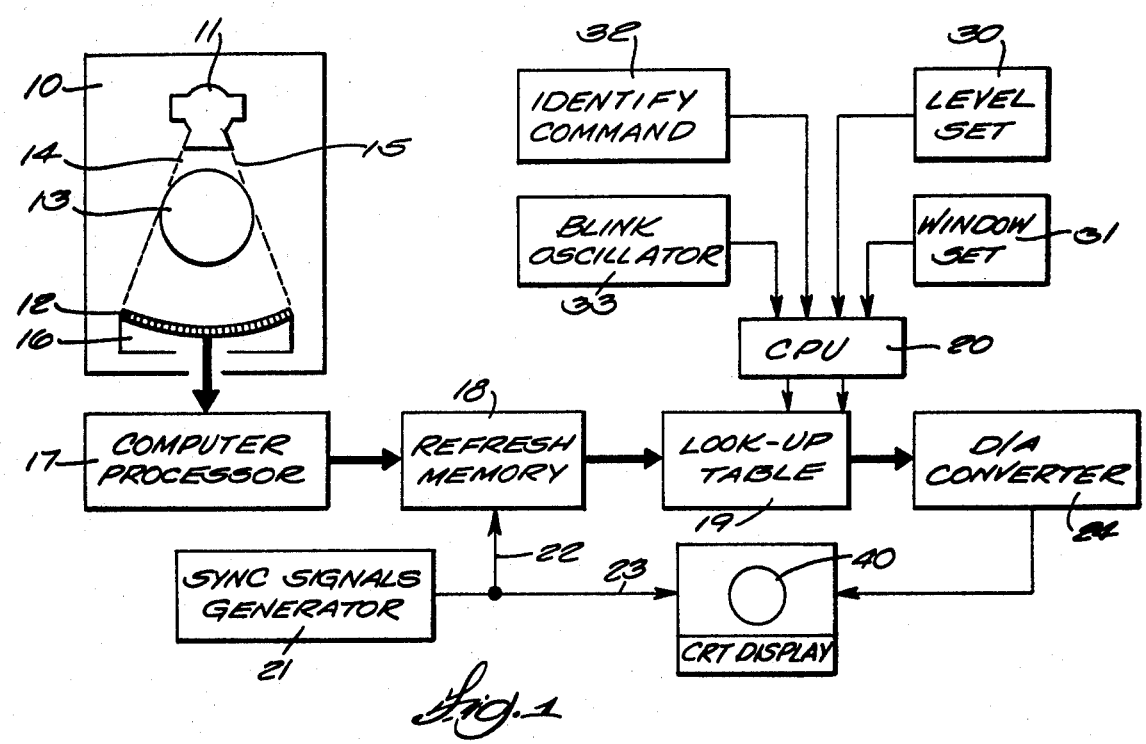
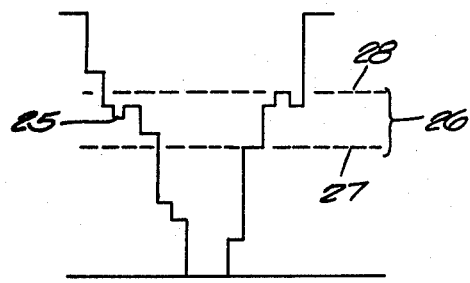
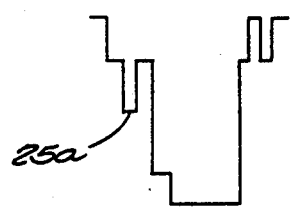

CT NUMBER IDENTIFIER IN A COMPUTED TOMOGRAPHY SYSTEM

BACKGROUND OF THE INVENTION

This invention relates to computed tomography and is particularly concerned with determining the CT numbers of zones of interest in an image displayed on a cathode ray tube which zones lie in the so-called level or center of the gray scale window.

In computed tomography, CT numbers are proportional to the X-ray attenuation by small volume elements in the body being scanned with an X-ray beam. A feature of the invention is to cause zones in the computer reconstructed image corresponding with a small range of CT numbers to blink in the context of the entire image or picture being displayed such that the CT numbers of the zones may be identified.

In computed tomography, X-ray transmission characteristics are measured along a plurality of paths through a body undergoing examination. Signals corresponding with the intensity of the X-rays in the various paths are processed by a computer which develops a matrix of CT numbers that govern the intensity or brightness of picture elements (pixels) which make up the displayed image. An illustrative method of image reconstruction with computed tomography is described in U.S. Pat. No. 3,778,614 to Hounsfield, which is incorporated by reference as background material in this disclosure.

A variety of algorithms had been developed for controlling a computer to convert X-ray attenuation data of each volume element in a layer of the body being examined with a scanned X-ray beam to a matrix of CT numbers that are usable to control a cathode ray display tube (CRT). X-ray attenuation by the volume elements is expressed as a CT number which is defined as follows:

$$CT \text{ number} = K\left[\frac{u_t - u_w}{u_w}\right]$$

where $u_w$ is the X-ray absorption coefficient of water and $u_t$ is the X-ray absorption coefficient of tissue.

The value of $K$ in this equation depends on the number of gray scale gradations into which the full absorption range is divided. For a system using 1024 gray scale gradations, $K = 500$. Systems using 256, 1024 and 2048 gray scale gradations or CT numbers have been used and higher ranges could be used.

The computed CT numbers are stored in a memory and, with a known type of display controller, their voltage analogs may be used as z signals to modulate the intensity of the beam in a raster scanned cathode ray tube for producing a visible image.

The detectors which are used for sensing the large amount of X-ray data and for providing intensity signals to the computer are extremely sensitive to X-rays. Using data provided by the detectors, the computer algorithm operates to produce a range of CT numbers with greater X-ray attenuation resolution or gray scale steps than can be distinguished by the human eye in a cathode ray tube display. For example, present tomographic image reconstruction methods are capable of quantitizing X-ray attenuation measurements into 1024 or more separate levels as indicated above. Cathode ray tubes, on the other hand, are typically incapable of displaying more than approximately 64 visually discernible shades or gray scale levels. Hence, it has been the practice to select from a large range of CT values, such as 1024, a limited range called a window and to display picture elements having CT values within the window over the gray scale capability of the CRT in which case CT values above the upper window limit are white and those below the lower window limit are black.

Significant medical information such as the presence or absence of tumors in soft tissue is often represented by minimal CT number differences. Those practicing the computed tomography art foresee the possibility of correlating the CT numbers of zones in the displayed image with the nature of the tissue involved and with the presence or absence of pathology in the tissue. For example, a benign cyst might fall within one small range of CT numbers and a malignant tumor or healthy tissue may fall within another range. If the relationship between CT numbers and the condition of tissue can be accurately correlated by further experience, a substantial diagnostic aid will be achieved.

Some computed tomography systems now in use provide for identification of CT numbers corresponding with particular zones in a displayed image. CT number identification in prior apparatus involves displaying the picture within a selected gray scale range or window. A level is selected which corresponds with the center of the gray scale within the window. A window is also selected which, by way of illustration and not limitation, could have an upper CT number limit of $+100$, corresponding with white, and a lower limit of $-100$, corresponding with black, in which case the gray scale would be expanded over a range of CT numbers equaling 200 and the center or level setting would be 0 in this example.

The prior procedure for determining the CT number of a zone of interest in a displayed image was to narrow the window down to a range of two CT values so that there would be one CT value at the level setting and one below it. Thus, the gray scale was compressed to two gradations, black and white, and all pixels in the displayed image on the screen of the display tube appeared either white or black. The level control could then be adjusted to a condition at which a particular zone of interest within the display would be caused to change from black to white. The level setting which caused this change could then be interpreted as the CT value of the zone of interest. If the CT number of any other zone was required, the level or center of the gray scale was set to correspond with it and the window was reduced or converged to this particular level. Again, any zone in the displayed picture with a higher CT number than that which corresponded with the level setting would appear white and any below the level setting would appear black so that the CT numbers corresponding with the level could be identified.

A disadvantage of the prior practice just described is that the zones whose CT numbers were sought to be identified could not be visualized in the context of the displayed image since when the window was reduced to the range of plus and minus one value relative to the set level, all picture information outside of that range was obliterated. That is, only island-like zones having CT numbers near the level setting were visible on the screen of the cathode ray tube. Another disadvantage was that the window had to be reset and the displayed picture reestablished before the radiologist could continue his study of the entire image.

In accordance with the present invention, the CT number of all zones in the visible displayed image having corresponding brightness or grayness may be determined within the context of the image on the screen of the cathode ray tube, that is, without obliterating the image or changing the window settings of the gray scale. This involves setting the center, called the level, of the gray scale window to correspond with the intensity or grayness of the zone of interest in the image. The window limits are selected previously. When CT number identification of any selected zone is desired, the operator simply presses an identification command button which causes all picture zones at the selected level to blink or turn white and then go back to normal gray level. When the selected zones blink to white, other zones comprising the image continue to be displayed in their normal gray scale and, of course, between blinks even the selected zones are displayed in their normal gray scale. The CT number is easily determined by simply reading the level setting which corresponds with the zone starting to blink.

Accordingly, a principal object of this invention is to provide a method and means for causing picture elements, in a cathode ray tube display of a computer reconstructed image, that correspond with the center of the gray scale or level, to blink for enabling rapid identification of the CT numbers of those pixels.

Another important object and feature of the invention is to provide for identifying the CT number of selected image zones in the context of the image itself without obliterating the remainder of the image and without the need for making any adjustments or settings to restore the displayed picture after using the blink mode.

DESCRIPTION OF THE DRAWING

FIG. 1 is a block disgram of a computed tomography imaging system in which identification of CT numbers is implemented;

FIG. 2 is an example of a high resolution analog signal output from a tomographic image computer; and FIG. 3 is an output signal from an analog signal processor which represents an expansion of a portion of the signal in FIG. 2 over the full gray scale of a display tube.

DESCRIPTION OF A PREFERRED EMBODIMENT

In FIG. 1, the components of an X-ray scanner for deriving X-ray attenuation data relative to small volume elements in a slice or layer of a body being examined are enclosed in a block marked 10. The scanner comprises an X-ray tube 11 and a curved array of X-ray detector elements 12. Disposed between the X-ray tube 11 and the detector array 12 is a body 13 that is subject to X-ray examination. X-ray tube 11 and detector 12 are on a common mounting for orbiting jointly around body 13. A thin fan-shaped X-ray beam having boundary rays 14 and 15 is projected through the body and the intensities of the rays in the beam, after having passed through the body, are sensed by detectors 12. In this illustrative scanner, the X-ray tube and detector are orbited and the X-ray beam is pulsed on and off for every small consecutive angular increment in a complete orbit. During each X-ray pulse, the X-ray intensities of the summation of elements along each ray path in a body layer are obtained by the multiple detector array 12 which produces corresponding analog signals.

A data acquisition system which is symbolized by a block marked 16 converts the analog signals to digital signals which are transferred to the memory of a computer processor that is symbolized by the block 17. When a full scan of the body 13 is complete, the computer processor computes binary CT numbers, having ten bits in this example, and there is a binary number for each volume element. The computed CT numbers are representative of X-ray attenuation by the volume elements in the body. Each volume element, as an example, may be 1.3mm square by 1cm thick. Ten digit binary numbers, however, are representative of more gray scale gradations than could be detected or perceived by the human eye so, as will appear, all numbers in a series representing the X-ray intensities of a body layer are normalized to six digit numbers which, after having been converted to analog signals, are used as z signals to modulate the intensity of a raster scanned cathode ray display tube. The CT numbers, in digital form, for each slice of the body that is scanned are usually stored in discs or magnetic tape memories associated with the computer processor 17 so that the numbers for each slice will be available for controlling the image display apparatus at any time that a study of an image is desired. The CT numbers for a slice or scanned layer of the body are read from the computer processor 17 into an adressable refresh memory matrix 18 which stores the numbers. In a typical commercial embodiment, the matrix is 320 × 320 in which case there are more than 100,000 digital CT numbers for each slice. Each number in the refresh memory matrix 18 has an $x$ and a $y$ coordinate and the value of each number is the $z$ value which, when converted to a corresponding analog voltage value, is used to modulate the intensity of the electron beam in a raster scanned cathode ray tube 40 with which the reconstructed X-ray image is displayed as will be discussed more fully later. By way of illustration, in a commercial embodiment CRT display 40 is refreshed with data stored in the refresh memory 18 sixty times per second. CT number data is read out of the refresh memory matrix serially or in a row after row fashion synchronously with the scan rate of the CRT 18. In one commercial embodiment, a Ramtek Model 9133 refresh memory is used. It is based on a prior Ramtek Model RM 9100.

The CT numbers generated by the computer and stored in the matrix range between −511 and +511 in this example and each is represented by a ten bit word. This range of CT numbers, however, is greater than the resolution of the remainder of the system including the cathode ray tube. The total of 1024 gray scale gradations could not be perceived by the human eye. Consequently, the ten bit words are converted to six bit words with the use of a look-up table 19 which, in this example, enables 64 shades of gray to be displayed ranging from black to white.

Although the number of shades of gray to be displayed is somewhat arbitrary, 64 shades of gray are assumed in this case as the number that can be perceived by the human eye. Thus, the look-up table 19, in this example, has six memory planes and cooperates with other components that are to be described by converting the ten bit numbers from the refresh memory 18 to six bit numbers which can represent 64 shades of gray.

At this juncture it is desirable to consider some identities which are pertinent to understanding operation of the system. As indicated above, the CT value range is normalized to permit display of up to 64 shades of gray, including black and white, depending on the window control setting. The intensity (I) value (0-63) of a particular pixel location can be determined if the data value (D), the level value (L) and the window value (2H) are known. The identities are as follows:

If $L + H \leq D, I = 63$

If $D < L - H, I = 0$

If $L - H \leq D < L + H, I = (32/H) \times [D-(L-H)]$

The I values are to be considered equivalent to relative voltage values of the output video signal to CRT 40 between blanking level or black (I = 0) and (I = 63).

L is the level setting for the center of the window and is expressed in terms of a CT number lying within the center of the displayed range. The full window height is 2H and the window is symmetrical about the level L.

Referring to FIG. 1 again, a CPU (central processing unit) 20 has the above mentioned identity algorithm in its instruction set. CPU 20 and look-up table 19 are instrumental in developing digital numbers which correspond with analog signals for controlling the z axis of the cathode ray tube display 40. CPU 20 and look-up table 19 cooperate to assign an intensity value that permits displaying a portion of the 1024 CT numbers with a scale of no more than 64 shades of gray. The intensity values depend on the computed CT numbers, the window values, and the level value.

Ten bit words are delivered from the refresh memory 18 to the look-up table 19 every 100 nanoseconds. All words are actually the addresses to the memory planes in the look-up table 19. In this example, the CPU is programmed to know that there are only 1024 possible CT numbers in the refresh memory for each body layer. Thus, prior to the time the ten bit number is put into the look-up table, the CPU looks at the value at which the level or center of the window is set and the value at which the window is set and it looks at all CT numbers and determines what z or intensity value the number should have to properly fit within a displayed gray scale of 64 possible shades. The CPU does this using the identities set forth above. The CPU turns out the intensity values in the form of digital numbers for any possible CT number. The rate at which the refresh memory 18 is read is synchronized with the beam scan rate of the cathode ray tube in CRT monitor 40. This is symbolized by a sync generator 21 having sync signal output lines 22 and 23 leading to the refresh memory 18 and monitor 40, respectively.

The intensity values or z signal values in digital form are delivered to a digital-to-analog converter 24 which produces analog output signals that control the z axis of monitor 40 in synchronism with memory readout. The output from the digital-to-analog converter 24 is actually a composite video signal which includes all of the synchronizing information.

The meaning of window and level settings will be briefly discussed in reference to FIGS. 2 and 3. FIG. 2 schematically represents a portion of an analog signal corresponding with the digital signal output from computer processor 17 which corresponds with CT numbers. The signal covers a wide dynamic range wherein a high density volume element in the body such as bone might have a CT number of around +500 and water, fat and air would have CT numbers of 0, −50 and −500, respectively. Soft tissues usually have values greater than 0, in the +10 to +40 range. Small range variations such as the one marked 25 within the large dynamic range signal waveform, often contain significant medical information in terms of tissue density variations which might, for example, indicate the presence of a tumor or other lesion. The limited gray scale of the cathode ray tube and the inability of the eyes to perceive a small variation would, however, obscure the presence of the variation 25 in the entire dynamic range of the signal of FIG. 2 if it were displayed on a cathode ray tube. Thus, a small portion or window is extracted from within the larger dynamic range of a signal and it is expanded to fill the gray scale. The center level and width of the window with relation to the overall signal may be adjusted to provide an optimum display. For example, if a signal within the dynamic range of the window 26 is expanded to fill the gray scale, the signal of FIG. 3 results. All signal levels below the base level 27 of window 26 are displayed at the minimum cathode ray tube intensity whereas all signal levels above the maximum threshold value 28 are displayed at maximum cathode ray tube intensity. Signal levels falling within the window 26 are expanded to fill the dynamic range of the cathode ray tube. The small signal variation 25 of FIG. 1 is thereby expanded to the large dynamic variation 25a of FIG. 3 and will thereby be made visible on a cathode ray tube display.

The position of the window 26 may be adjusted to provide high resolution displays in various portions of the overall signal. There are corresponding CT numbers for the lower and upper limits 27 and 28 of the window, respectively. The level, or a point half way between limits 27 and 28, also corresponds with a CT number.

Referring again to FIG. 1, the six digit binary numbers respectively representing one of 64 shades of gray are outputted from look-up table 19 to a digital-to-analog converter 24 wherein th digital signals are converted to successive analog video signals at the sweep rate of the CRT display tube 40. As indicated earlier, a sync signal generator 21 supplies sync signals for readout of the refresh memory 18 via cable 22 and the sync signals become part of the composite video signal which leaves the digital-to-analog converter and is used to drive the CRT display 40.

The equipment and functions thus far described are basically those which are involved normally in producing a reconstructed image of a body layer on the screen of a raster scanned CRT for visualization and study. The equipment and functions involved in the new way of identifying the CT numbers of any zone or zones in the displayed image by causing any selected zone to blink to white and back to its normal shade of gray in the context of the image will be discussed next.

An identity which is pertinent to blink mode CT number identification is:

$L \pm (H/16)$ where L is the window level which, by definition, is the CT number at the center of the gray scale in the selected window and H is the span of the window in terms of CT numbers from the plus limit down to L and from the minus limit up to L. In other words, the total window height or span is equal to 2H. This identity expresses the CT value range whose corresponding picture elements or zones will be blinked during the CT number identification mode of operation. The divisor or denominator 16 in the identity is somewhat arbitrary and could have smaller or larger values but this divisor has been found suitable through experience with a commercial embodiment. The number of CT values to be blinked is preferably a minimum of one with a rounding off of larger odd numbers. By way of example and not limitation, a typical relationship between the window height and the CT value range to be blinked is set forth in the following tabulation:

| Window (H) | 10 | 20 | 30 | 40 | 50 | 75 | 100 | 150 | 250 | 500 |
|---|---|---|---|---|---|---|---|---|---|---|
| Blink Width | 1 | 3 | 3 | 3 | 5 | 5 | 7 | 11 | 17 | 33 |

Referring again to FIG. 1, the CPU 20 has the last stated as well as the earlier stated identity in its instruction set or program. Manually controllable means 30 are provided for supplying the CPU with a signal corresponding with any particular window level and manually controllable means 31 are provided for supplying a signal corresponding with the window height, +H and −H, relative to the CT number of the level. A block 32 symbolizes providing the CPU with a CT number identification command signal. As far as the operator is concerned, simply pressing a self restoring push button or rocker switch is all that is necessary to enable identification by initiating blinking. An oscillator 33 is also provided for blinking CT values at the set window level so, as an example, the blinked pixels go white for about 250 milliseconds and return to normal gray value for about 500 milliseconds on a continuous basis as long as the identify command persists.

Assuming now that the window has been set and that the identification command is initiated, an output signal is produced by oscillator 33 and it is furnished to the CPU. When the oscillator output is in one state such as low, the CPU satisfies the identities first presented herein and the picture elements are displayed in their normal gray scales on the CRT. When the oscillator goes high, the CPU 20, which has address and data buses, matches the 10 bit words from the refresh memory to the 10 bit level and the CPU changes all words at the corresponding level in the look-up table 19 to a value corresponding with a white video signal. The level may be adjusted during the blink mode in which case picture elements having CT numbers agreeing with the current level setting will blink. In any case, when the desired zones blink it is only necessary to read off the level setting at that time to determine the CT number corresponding with the zones. Actually, as is evident from the tabulation given above, a small range of CT values will blink for each level setting as a result of the CPU executing the last identity given above.

In some systems cathode ray tube monitors are used which display the image in a color scale rather than a gray scale as when a black and white monitor or display is used. In applying the blink mode of CT number identification to such systems any color in the spectrum corresponding to the level setting may be caused to switch or blink to a particular unique color to enable identification.

Although the new blink mode for CT value identification has been described in substantial detail, even using specific numbers for the sake of demonstration, such description is to be considered illustrative to those skilled in the art rather than limiting, for the invention may be variously implemented and is to be limited only by construing the claims which follow.

We claim:

1. In a computed tomography system including means for producing first electric signals having a large range of values corresponding respectively with the X-ray attenuation and CT numbers of volume elements in a layer of a body; a memory matrix for storing said signals; display means for displaying a visual image depending on said stored signals comprising an intensity modulatable scanning cathode ray tube and means for modulating the intensity of said tube in correspondence with the values of successive signals; means for selecting from said large range of signal values signals lying within a window comprised of a smaller range of values defined by upper and lower limits and a level value centered between said limits; means for converting said signals within said window to signals for modulating said cathode ray tube; and, improved means for identifying the CT numbers corresponding with selected zones in said displayed image comprising:
   means for selecting signals in a narrow band corresponding substantially with the CT number values of said level within the selected window;
   means for activating said selecting means; and
   means for causing said selected signals to modulate only those zones in said displayed image which have CT numbers corresponding substantially with said selected level to an intensity corresponding with said level and alternately in quick succession to higher intensity whereby to enable identification of the CT numbers.

2. In a computed tomography system including means for producing first electric signals having a large range of values corresponding respectively with the X-ray attenuation and CT numbers of small volume elements in a layer of a body;
   an intensity modulatable raster scanned cathode ray display tube;
   memory means for storing said first signals in a matrix suitable for refreshing said cathode ray tube;
   signal processor means including means for producing second signals corresponding with intensities of zones in said image by selecting from said large range a smaller range of values within a window having a center value designated as its level (L) and having a height of (2H) where H represents upper and lower limit values which are symmetrical, respectively, about said level;
   means responding to said second signals by controlling the intensity of said display tube; and
   means for selectively controlling said means for producing said second signals to convert signals corresponding with the selected level to signals which cause only corresponding zones in said image to be modulated repeatedly to maximum intensity and alternately in rapid but perceptible succession to an intensity corresponding with the level value whereby to enable identifying the CT numbers by determining said level.

3. The apparatus as in claim 2 wherein said processor is programmed to selectively execute the identities:

if $L + H \leq D$, $I =$ maximum if $D < L - H$, $I = 0$ if $L - H \leq D < L + H$, $I = \frac{\text{number of possible gray scale values in the display}}{2H} [D - (L - H)]$ where D is data corresponding with any first signal value and I is the intensity value corresponding with said data.

4. The apparatus as in claim 3 wherein the gray scale has 64 1 possible values.

5. The apparatus in claim 2 including oscillator means for producing pulses corresponding with the duration of said maximum intensity.

* * * * *